United States Patent [19]

Self

[11] Patent Number: 4,956,303

[45] Date of Patent: Sep. 11, 1990

[54] SECONDARY ANTIBODIES AGAINST COMPLEXES OF SMALL MOLECULES AND BINDING PARTNERS THEREFOR, THEIR PREPARATION, AND THEIR USE IN DIAGNOSTIC METHODS

[75] Inventor: Colin H. Self, London, United Kingdom

[73] Assignee: Antibody Technology Limited, United Kingdom

[21] Appl. No.: 43,377

[22] Filed: Apr. 28, 1987

[51] Int. Cl.$^5$ ............................................. G01N 33/537
[52] U.S. Cl. ..................................... 436/542; 436/507; 436/518; 436/538; 436/545; 436/548; 530/387
[58] Field of Search ............... 436/507, 817, 823, 824, 436/548, 545, 518, 538, 542, 804; 530/387

[56] References Cited

U.S. PATENT DOCUMENTS

| | | | |
|---|---|---|---|
| 3,839,153 | 10/1974 | Schuars | 435/7 |
| 3,933,997 | 1/1976 | Hersh | 436/804 X |
| 4,298,592 | 11/1981 | Lin | 436/539 X |
| 4,544,640 | 10/1985 | Soma | 436/512 X |
| 4,606,855 | 8/1986 | Deutsch | 530/387 |
| 4,659,678 | 4/1987 | Forrest | 436/548 X |

FOREIGN PATENT DOCUMENTS 1587193 1/1981 United Kingdom .
2113713A 10/1983 United Kingdom .
2161165A 8/1986 United Kingdom .
2171999A 10/1986 United Kingdom .

OTHER PUBLICATIONS

International Publication No. WO 85/04422.
International Publication No. WO 86/00140, Self, 1/3/86.
Nemazee, D. A. et al., "Enhancing Antibody: A Novel Component of the Immune Response", PNAS, vol. 79, pp. 3828–3832, 1982.

Primary Examiner—Robert J. Hill, Jr.
Attorney, Agent, or Firm—Jacobs & Jacobs

[57] ABSTRACT

A secondary antibody capable of stabilizing the binding of a small molecule to its binding protein is described which secondary antibody is capable of binding said binding protein in the presence of an in the absence of the small molecule but is not capable of binding said small molecule in the absence of binding protein. Such antibodies may be obtained by forming a complex between a small molecule and its binding protein, using the complex to raise antibodies and selecting the antibodies. The antibodies may be used in competitive assays in which it is desired to improve the binding of a small molecule or labelled small molecule to its binding protein.

19 Claims, No Drawings

SECONDARY ANTIBODIES AGAINST COMPLEXES OF SMALL MOLECULES AND BINDING PARTNERS THEREFOR, THEIR PREPARATION, AND THEIR USE IN DIAGNOSTIC METHODS

The present invention relates to a class of secondary antibodies which can stabilise the binding of small molecules by their binding proteins, to the preparation of such secondary antibodies, to their use in diagnostic tests such as competitive assays and to diagnostic kits which contain them.

My European Patent Application Nos. 85901495 and 8590319 disclose inter alia a class of secondary antibodies which can bind a complex of a small molecule and its primary antibody but which cannot bind either the small molecule or its primary antibody in the absence of the other. The disclosure of said European Patent Applications are incorporated herein by cross reference. A new class of secondary antibodies has been discovered which offers many of the advantages of the known class of secondary antibodies coupled with an easier method of preparation The present invention provides a secondary antibody capable of stabilising the binding of a small molecule to its binding protein which secondary antibody is capable of binding said binding protein in the presence or absence of said small molecule but is not capable of binding said small molecule in the absence of said binding protein.

Thereinafter such secondary antibodies will be referred to as "trapping antibodies". Such trapping antibodies generally have a k value of less than $10^3$ (and preferably less than $10^2$) with respect to the small molecule and have a k value of at least $10^5$ (and preferably $10^6$) with respect to the binding protein or complex of small molecule and binding protein.

The binding protein may be an antibody, enzyme or other receptor which binds the small molecule which binding is preferably specific to the small molecule. The antibody may be monoclonal or polyclonal. Monoclonal antibodies may be preferred for uniformly in use but polyclonal antibodies offer great advantages in terms of ease of preparation. The antibody may be the complete immunoglobulin or a fragment thereof (for example the $F_{ab}$ or $F(ab')_2$ fragment) which retains binding function. The enzyme may be a binding enzyme such as dihydrofolate reductase. Other receptors include hormone receptors and the like. The binding protein is preferably a homogenous preparation with respect to materials which bind the small molecule. A suitable example of a small molecule which binds to an enzyme is methotrexate which binds to dihydrofolate reductase.

The binding protein employed in this invention is most suitably an antibody and is most preferably a monoclonal antibody. Thus in a preferred embodiment the present invention provides a secondary antibody capable of stabilising the binding of a small molecule to its primary monoclonal antibody which secondary antibody is capable of binding said primary monoclonal antibody in the presence or absence of said small molecule but is not capable of binding said small molecule in the absence of said primary monoclonal anitbody.

The trapping antibody may be polyclonal or monoclonal but is preferably monoclonal. The trapping antibody may be an antibody fragment (such as the Fab or F(ab')$_2$ fragment) as long as it retains its binding ability The primary monoclonal antibody may also be an antibody fragment (such as the Fab or F(ab')$_2$ fragment).

The small molecule may have a molecular weight of for example 100 to 1500, more suitably from 120 to 1200 and favourably from 200 to 1000. The small molecule may aptly be a steroid, medicament, drug of abuse, amino acid, peptide, carnatine, carbohydrate, environmental pollutant or the like. Very suitably the small molecule is a steroid such as progesterone, oestradiol, oestratriol, oestrone sulphate, hydrocortisone, cortisone, testosterone, oestrogen or the like. Very suitably the small molecule is a medicament such as theophylline, digoxin or an aminoglycoside antibiotic such as gentamicin. Very suitably the small molecule is a drug of abuse such as morphine, cocaine or the like.

Most aptly the trapping antibody is provided free from interfering substances such as small molecules especially those of related structure to that to the assayed (such as steroids, medicament, drugs of abuse and the like). Occasionally polyclonal trapping antibody can be contaminated with small amounts of polyclonal overlap antibodies (see my aforementioned European Patent Specifications) but this will generally not matter and in any event such contamination can be prevented by using appropriate selection techniques (vide infra). Most aptly the trapping antibody is in solid form. Favourably the trapping antibody is in the form of a freeze dried solid. Desirably the trapping antibody is provided within a closable container.

The trapping antibody of this invention may be made by the methods disclosed in my European Patent Applications referred to hereinbefore but changing the antibody selection process to select antibodies which bind the primary antibody and which stabilise the binding of the small molecule to its primary monoclonal antibody.

Any method of selection can be employed which demonstrates the binding between the small molecule and its primary monoclonal antibody; for example a method which shows the equilibrium or a method which shows the stability of complexes with and without the trapping antibody.

A suitable method of selection comprises separating antibody from an antiserum and employing it is the following method. The primary monoclonal antibody is bound to the wells of microtitre well strips (strips made up of a single row of wells such that individual wells may be snapped off and placed in a standard scintillation vial containing suitable scintillation fluid and any radioactivity they contain counted). A standard amount of radio-labelled small molecule is added to all of the wells. Then to half of the wells is added a standard amount of the test antibody preparation and to the other half a control antibody preparation derived from immunisation with an unrelated antigen. The wells are incubated and then shaken and washed free of unbound materials. They are then filled with a solution containing a large excess (relative to the amount of small molecule binding protein on the wells) of unlabelled small molecule. This is time zero at which one set of wells are immediately taken and shaken and washed free of unbound contents. At set times (such as ten minute intervals) thereafter sets of wells are similarly treated. The retained radioactivity of the wells is measured and the results plotted showing the effect of the added trapping antibody (if present). plots showing increased radioactive counts indicates the presence of a trapping antibody in the original antiserum. The presence of trapping antibody in monoclonal preparations may be similarly demonstrated. Appropriate antisera or preparations may be used as a source of trapping antibody The solid and/or purified antibody may be obtained from the appropriate antisera or preparation by any convenient method.

The trapping antibodies of this invention may be used in methods of qualitative or quantitative determination of the small molecule. Normally the determination method is a competitive assay and favourably is one in which a detectable small molecule is employed. Preferably the small molecule is detectable by being isotopically labelled, for example labelled with a radio isotope or an isotope detectable by nuclear or electronic spin, for example by nmr or esr.

In a favoured further aspect this invention provides a method for the quantitative determination of a small molecule which method comprises employing a trapping antibody of this invention in a competitive assay wherein labelled small molecule is isotopically labelled The trapping antibody stabilises the binding of the small molecule to its primary monoclonal antibody thereby giving rise to a higher signal. This can be attributed to such factors as improved stability to washing and the like.

Determinations will normally take place in aqueous solution under conventional non-extreme conditions, for example at 2° to 56° C., more usually at 4° to 40° C., favourably at 10° to 37° C. and preferably at ambient temperature. The pH employed is generally from 4 to 10, more aptly from 5 to 9 and preferably at approximately neutral pH.

In such tests generally the sample to be determined is exposed to the primary monoclonal antibody, the isotopically-labelled small molecule simultaneously or subsequently added, the mixture incubated the trapping antibody added and the mixture incubated, the bound labelled small molecule separated from the unbound labelled small molecule and the amount of bound and/or unbound radioactivity measured. Standard samples (for calibration and comparison) are similarly performed.

In a less favoured alternative the trapping antibody can be added at the same time as, the labelled small molecule.

The separation of the bound radio labelled small molecule may be by virtue of the primary monoclonal antibody being bound to a surface and separating the liquid from the solid phase or alternatively by precipitation methods, for example by adding a precipitating antibody and separating the liquid from the solid phase.

In such methods the small molecule is most suitably isotopically-labelled, for example a steriod, labelled with a tritium or $C^{14}$.

Many competitive assays are available for the determination of molecules. Many of these existing systems are effective but in general it would be an advantage if they could be made more effective. A method has now been found which can offer improvements such as improved sensitivity, range, speed or specificity. In addition the new method offers the opportunity of assaying small molecules in a particularly favourable manner.

Accordingly the present invention provides a competitive assay for a small molecule which comprises:
  (a) introducing the sample of the small molecule to be determined and an amount of a labelled small molecule to a receptor for said small molecule in a manner which allows competition for the receptor to occur
  (b) separating bound labelled small molecule from unbound labelled small molecule
  (c) determining that fraction of the labelled small molecule which is bound or unbound; characterised in that
  (d) a trapping antibody is employed to improve the binding of the small molecule and the labelled small molecule to the receptor.

When used herein the term "competitive assay" means an assay in which a small molecule and a labelled small molecule compete for a receptor and the amount of labelled small molecule which becomes bound to the receptor is used to indicate the amount of small molecule in the sample being determined; in such an assay the competition between the small molecule and the labelled small molecule may be simultaneous or sequentional or both and the amount of labelled small molecule bound may be determined by measuring the bound labelled small molecule or the labelled small molecule which has not become bound. The use of the term "competitive assay" in this way is common. The "receptor" may be any binding protein as hereinbefore indicated. Most suitably the receptor is an antibody and is preferably a monoclonal antibody. The antibody may be the complete immunoglobulin or a fragment thereof.

Either or both the bound or unbound labelled small molecule may be determined. This normally takes place after separation of the phases.

The label applied to the small molecule may be any which does not prevent the labelled small molecule from competing with the small molecule for the receptor. Thus for example enzyme labels, fluorescent labels, chemiluminescent labels, coenzyme labels and isotopic labels may be envisaged.

The isotopic label used in the labelled small molecule employed in this invention may be any which is detectable, for example an isotope detectable by virtue of radioactive decay, by virtue of its nuclear spin or electronic spin (whether natural or induced) or by virtue of its magnetic moment.

One class of particularly suitable isotopic labels is that which involves replacement of an atom in a small molecule by the same chemical atom of different atomic number.

A second class of particularly suitable isotopic label involves replacement of an atom by a chemical distinct atom, for example replacement of hydrogen by fluorine or iodine.

Particularly apt isotopic labels detectable by virtue of their radioactive decay include $H^3$ and $C^{14}$.

The advantages of employing a label such as $H^3$ and $C^{14}$ lie in their well understood behaviour as labels which enable them to be used routinely in laboratories. This method of detection has the advantage that it may be readily adapted to automatic assay methodology and that the labelled small molecule competes for the receptor in exactly the same manner as the unlabelled small molecule.

The enzyme label employed in labelled ligand of this invention may be any which is capable of giving rise to a determinable signal by virtue of its enzymic activity. Typical enzymes employed for this purpose include phosphatase, peroxidase and β-galactcsidase and the like. The skilled worker will be aware of the widespread use of such enzymes as labels. The enzyme may be attached to the ligand in any convenient manner, for example by covalent attachments or by complex formation with a material bound to the ligand such as an antibody or component thereof such as a Fab fragment Suitable fluorophors for use as labels include classical fluorophors and lanthanide based fluorophors such as the europium chelate fluorophors.

Suitable chemiluminescent agents for use as labels include classical luminol derivatives and the newer aryl acridinium ester labels.

Suitable cofactor labels for use include flavin adenine dinucleotide, nicotinamide adenine dinucleotide and like groups which can be employed as enzyme prosthetic groups.

In a particularly preferred aspect the present invention provides a competitive assay for a small molecule which comprises:

(a) introducing the sample of the small molecule to be determined and an amount of a labelled small molecule to monoclonal antibody for said small molecule in a manner which allows competition for the monoclonal antibody to occur, (b) separating the bound labelled small molecule from the unbound labelled small molecule, (c) determining that fraction of the labelled small molecule which is bound or unbound; characterised in that (d) a trapping antibody is employed to improve the binding of the small molecule and the labelled small molecule to the monoclonal antibody.

The trapping antibody may be used at any stage of the competitive assay where it is desired to improve the binding of the small molecule or labelled small molecule to the receptor. However, it is preferred that the trapping antibody is employed after the competition between the small molecule and labelled small molecule has taken place.

Thus in a preferred aspect the present invention provides a competitive assay for a small molecule which comprises:

(i) introducing the sample of the small molecule to be determined and an amount of a labelled small molecule to a monoclonal antibody for said small molecule in a manner which allows competition for the monoclonal antibody to occur, (ii) introducing a trapping antibody to improve the binding of the small molecule and the labelled small molecule to said monoclonal antibody, (iii) separating the bound labelled small molecule from the unbound labelled small molecule, and (iv) determining that fraction of the labelled small molecule which is bound or unbound.

As previously indicated for the competition step the small molecule and labelled small molecule can be introduced to the receptor simultaneously or sequentially. I prefer to add the sample prior to addition the labelled small molecule. The competition step can take from a few seconds to many hours as is well understood for competition assays but I believe it is most suitable that this step takes a short time such as several seconds to a few hours and in general from about 15 seconds to 1 hour, more usually from about 30 seconds to 20 minutes, for example 1 to 10 minutes.

The trapping antibody is aptly introduced at the end of period allowed for competition. Enough trapping antibody is normally added to saturate most and preferably essentially all of the original monoclonal antibody (with respect to the small molecule receptor). Again this step can take place from a few seconds to many hours but I believe it is most suitable that several seconds to a few hours are employed and in general from about 15 seconds to 1 hour, more usually from about 30 seconds to 20 minutes, for example 1 to 10 minutes are allowed for this trapping stage. Generally the more trapping antibody employed the shorter the incubation period tends to be.

Both the competition and trapping stages may be carried out under conventional "physiological" conditions, for example at 2° to 56° C., more usually at 4° to 40° C. It has proved advantageous to employ depressed temperatures such as 4° C. for trapping but 10° to 37° C. is also favourable and ambient temperature is often both suitable and convenient. The pH employed is normally from 4 to 10, more aptly from 5 to 9 and preferably at approximately neutral pH. Buffers and tonicity adjusting agents may be employed if desired. Conventional buffers and tonicity adjusting agents are acceptable.

If desired the trapping antibody may be present in wash solutions employed in the assay procedure. This is believed to offer many advantages in terms of fixing.

The separation of the bound and unbound labelled small molecule may be carried out in any convenient manner, for example by immobilizing the bound labelled small molecule on a solid. The solid may be the surface of a container such as a tube or depression in a plate or the solid may be a particle suspended in the medium such as a filtrable particle, a centrifugable particle or very desirably a magnetic particle or the like. Aptly the monoclonal antibody is immobilized on a surface and the labelled small molecule becomes immobilized by virtue of binding to the immobilized monoclonal antibody. This is conventional and well known in the art. The bound and unbound labelled small molecule can thus be separated by separating the liquid medium from the solid surface. If the detection method employed requires it, the immobilized and free components may now be separated. The amount of label associated with the surface and/or with the small molecule may now be determined.

If desired any washing solutions employed to wash unbound label from the solid surface may include trapping antibody.

A benefit of employing a trapping antibody of this invention is that the washing steps in the assay can become less critical.

The trapping antibodies of this invention may be obtained by forming a complex between a small molecule and its binding protein, using that complex to raise antibodies and selecting the trapping antibodies. Selection methods are described hereinbefore.

Repeated immunisations may be employed to raise antibodies if desired. In some circumstances it may be sufficient to administer the binding protein but in general it is preferred to preform the complex, for example by thoroughly mixing together the small molecule and binding protein in aqueous solution or suspension optionally together with buffers and optionally together with surfactants.

As previously indicated by earlier European Patent Applications (and their equivalent U.S. Ser. Nos. 803137 and 832710 incorporated herein by cross-reference) may be read herewith.

The following examples are illustrative of the invention.

EXAMPLE 1

Trapping Antibody Against Oestradiol

A rabbit was immunised by multiple intradermal injection on a large shaved area of the back (20 each side) with the following mixture - 100 ug of anti-oestradiol monoclonal antibody (purified IgG obtained by conventional purification on an affinity chromatography column containing protein A) in 200 ul of 50 mM Tris buffer pH 7.4 mixed with 50 ug of oestradiol in 800 ul of the same buffer, incubated at R.T. (22° C.) for 30 minutes and the mixture then emulsified to form a water in oil emulsion with an equal volume (1 ml) of complete Freund's adjuvant. Twelve days after the animal received a further 200 ug of oestradiol alone in Tris buffer divided into ten subcutaneous injections on the back. After a further ten days a further boost was carried out by intramuscular injection (flank muscles) with the following mixture: 100 ug of the same monoclonal antibody against oestradiol in 100 ul of Tris buffer mixed with 800 ug of oestradiol in 800 ul of Tris buffer and incubated for 30 minutes at R.T. and then emulsified with 900 ul of incomplete Freund's adjuvant. The rabbit was bled to obtain trapping antibody as follows: Bleed 1-7 days post first injection, bleed 2-7 days post second injection; bleed 3-7 days post third injection.

In outline the determination was carried out as follows: The primary monoclonal antibody against oestradiol was absorbed onto plastic wells. The wells then received a given amount of labelled oestradiol and antiserum (either from the above bleeds or from a pre-immunisation bleed). All wells were shaken free of solution, washed and cold (unlabelled) oestradiol added. The 'zero time' wells were them immediately shaken free of solution and washed four times. The remaining labelled oestradiol was then determined in each well by scintillation counting. Over the next one four further wells were treated similarly to determine the rate of dissociation of the labelled oestradiol from the primary antibody.

The conditions of the example are as follows: 200 ul primary monoclonal antibody against oestradiol in 50 mM bicarbonate buffer pH 9.6 was placed in each well of a series of removawell strips (Immunon 2 obtained from Dynatech laboratories) and incubated at 37C for two hours. The solution was then removed and the wells glazed with 200 ul of 0.2% BSA in the same buifer for 1 hour at room temperature (R.T.). The glazing solution was removed and the wells washed four times with 50 mM Tris pH 7.4 containing 0.2% BSA and 0.02% Tween 20 (TBT). 180 ul of labelled oestradiol (containing 10,000 cpm and obtained from Amersham International plc 2,4,6,7-3H Oestradiol TRK. 322 95Ci/mmol) in 50 mM Tris buffer at pH 7.4 and the wells incubated for one hour at R.T. 20 ul of pre-bleed serum was added to a series (12) of wells or 10 ul of the Tris buffer followed by 10 ul of each of the antisera to be tested in each of a series of wells. They were then incubated for a further hour at R.T. The solutions shaken out and the wells washed four times with TBT. 200 ul of 100 ul/ml unlabelled oestradiol on Tris buffer was then added, incubated for one hour, their contents shaken out and the wells washed four times with TBT. The individual wells were then placed in individual scintillation vials containing 5 ml of scintillation fluid and their tritium content determined The results are as shown in Table 1 and indicate the increased power of the antisera to afford protection of the complex.

TABLE 1

| Sample | Count |
|--------|-------|
| Pre-bleed | 250 |
| Bleed 1 | 320 |
| Bleed 2 | 520 |
| Bleed 3 | 630 |

Bleed 3 was taken and the trapping antibody purified from it by using chromatography on a protein A column.

EXAMPLE 2

Use of Trapping Antibody Against Oestradiol

Microtitre well strips (Dynatech Immulon II) were coated with a monoclonal antibody against oestradiol (made by conventional techniques against a complex of oestradiol and BSA) by leaving 200 ul of a solution containing lug of the antibody in 50 mM bicarbonate buffer pH 9.6 in each well for 2 hours at 37 C. The solution was then shaken out and replaced with 0.2% casein in the same buffer and left for a further 1 hour at room temperature (21 C.). The wells were then washed with 50 mM Tris pH 7.4 containing 0.02% Tween 20 with four washes. A standard solution containing 50 ug of oestradiol per ml was made in 50 mM Tris pH 7.4. From this a range of concentrations from zero to 1 ug per ml were made and 180 ul of each of these added in duplicate to individual wells. The wells were incubated for 30 minutes at room temperature. Tritiated oestradiol (2,4,6,7-3H Oestradiol 95Ci/mmol TRK.322 Batch 75 Amersham International plc) was then added to each well - 20 ul containing 0.1 uCi (ca. 100,000 cpm). The wells were then incubated for 15 minutes at room temperature after which 10 ul of trapping antibody (IgG fraction purified from antisera by normal protein A absorption of Example 1) was added to each well. A similar series of wells received 10 ul of an unrelated antibody. The wells were incubated for a further one hour at room temperature. The solutions were shaken out and the wells washed twice with 50 mM Tris pH 7.4 containing 0.02% Tween 20. Ten ug of unlabelled oestradiol in 200 ul of 50 Tris pH 7.4 was then added to each well and the wells incubated for thirty minutes at room temperature. The solution was shaken out and the wells washed four times with 50 mM Tris pH 7.4 containing 0.02% Tween 20. The wells were then separated from each other and placed in scintillation vials containing fluid and their radioactivity counted.

Table 2 shows the results obtained with and without the trapping antibody. The addition of trapping antibody gives rise to a greater amount of binding of the labelled material and a steeper standard curve improving the characteristics of the assay. The difference is particularly marked at low concentrations of small molecule.

TABLE 2

| | counts per minute | |
|---|---|---|
| wt oestradiol/ml | Control | Trapping antibody |
| 1 μg | 120 | 162 |
| 100 ng | 168 | 350 |
| 10 ng | 355 | 498 |
| 1 ng | 481 | 805 |
| 100 Pg | 546 | — |

TABLE 2-continued

| | counts per minute | |
|---|---|---|
| wt oestradiol/ml | Control | Trapping antibody |
| 10 Pg | 560 | 848 |
| 1 Pg | 610 | 932 |
| 0 | 725 | 1138 |

EXAMPLE 3

Trapping Factor for Progesterone

A rabbit was immunised as follows: Multiple intradermal injections on a large shaved area of the back (20 each side) with the following mixture - 1 ml of incomplete Freund's adjuvant containing 2.5 mg of progesterone (shaken until dissolved) emulsified with 100 ug of monoclonal anti-progesterone antibody in 100 ul ascites fluid made up to 1 ml of 50 mM Tris pH 7.4 to form a water in oil emulsion. Two months after this the animal received a further 200 ug of progesterone in 0.75 ml of complete Freund's adjuvant with 100 ug of the monoclonal antibody in 0.75 ml of phosphate buffered saline as 0.5 ml in one foot pad and 0.5 ml in each flank intramuscularly. Ten days later 100 ug of progesterone in 200 ul of incomplete Freund's adjuvant with 250 ug of the monoclonal in 200 ul pBS were injected in the region of the popliteal lymph node.

The rabbit was bled to obtain trapping antibody as follows: Bleed 0 - pre-bleed prior to immunisation, Bleed 1-14 days after the first injection. Bleed 2-5 weeks after the first injection (not subsequently used), Bleed 3-7 weeks after the first injection, Bleed 4 immediately before the third injection (not subsequently use), Bleed 5-7 days after the third injection, Bleed 6-14 days after the third injection.

In outline the determination of trapping antibody was carried out as follows. The primary monoclonal antibody against progesterone was absorbed onto plastic wells. The wells then received a given amount of labelled progesterone and antiserum (either from the above bleeds or from a pre-immunisation bleed or from a bleed from a rabbit immunised with an unrelated immune complex). All wells were shaken free of solution, washed and cold (unlabelled) progesterone added. The 'zero time' wells were then immediately shaken free of solution and washed four times. The remaining labelled progesterone was then determined in each well by scintillation counting. Over the next hour further wells were treated similarly to determine the rate of dissociation of the labelled progesterone from the primary antibody.

The conditions of the example are as follows: 200 ul primary monoclonal antibody against progesterone in 50 mM bicarbonate buffer pH 9.6 was placed in each well of a series of removawell strips (Immunon 2 obtained from Dynatech Laboratories) and incubated at R.T. overnight. The solution was then removed and the wells washed four times with 50 mM Tris pH 7.4 containing 0.02% Tween 20 (TT). 190 ul of labelled progesterone (containing 100,000 cpm and obtained from Amersham International plc 1,2,6,7,3H progesterone TRK 413 91Ci/mmol) in 50 mM Tris buffer at pH 7.4 was added and the wells incubated for 30 minutes at R.T. 10 ul of each antiserum was added each to a series (12) of wells. They were then incubated for a further hour at R.T. The solutions were shaken out and the wells washed four times with TT. 200 ul of a saturated solution of progesterone made in Tris buffer by placing 5 mg of progesterone in 10 ml of buffer and incubating this mixture at 60C. with agitation for one hour was then added and incubated for 30 minutes. The wells were detached from each strip their contents shaken out and the wells washed four times with TT. The individual wells were then placed in individual scintillation vials containing 5 ml of scintillation fluid and their tritium content determined.

The results are as shown in Table 3 and indicate the increased power of the antisera to afford protection to the progesterone anti-progesterone complex. When the protective factors were tested in terms of their power to protect the association of progesterone and a different monoclonal antibody against progesterone no protective influence was observed.

TABLE 3

| Sample | Count |
|---|---|
| Controls (average) | 40 |
| Bleed 1 | 210 |
| Bleed 3 | 300 |
| Bleed 5 | 325 |
| Bleed 6 | 650 |

Bleed 6 was subsequently used to prepare isolated freeze dried trapping antibody against progesterone by protein A chromatography. The purified solid trapping antibody (10 mg) was dissolved in buffer (50 mM Tris pH 7.4 containing 0.1% casein) (100 mls), and dispersed into 100 vials. The contents of the vials were freeze dried and the vials capped.

EXAMPLE 4

Purified Trapping Antibody Against Oestradiol 5 ml of antiserum is taken and made up in a sodium sulphate solution to 18% sodium sulphate at 25° C. and left for 30 u minutes. A precipitate forms and is obtained by centrifugation and then dissolved in 2.5 ml of distilled water. A solution of 27% sodium sulphate is then added (to make the solution 14% in sodium sulphate). this is left at 25° for 30 minutes and the resulting precipitate obtained by centrifugation and then dissolved in 1.5 ml of distilled water. The solution is then dialysed against phosphate buffered saline at pH8 for 2 days.

A 5 ml column of protein A - Sepharose CL-4B is made and equilibrated with phosphate buffered saline at pH 8. One fifth of the solution from the dialysis is applied slowly to the column and the column washed with 50 ml phosphate buffered saline at pH 8. The antibody was eluted off with a 1M solution of acetic acid and the fractions coming off the column tested for protein content at 280 nm and for its trapping antibody content (by its ability to stabilise oestradiol and its primary monoclonal antibody). The rest of the dialysate was similarly treated.

They were further purified by applying to a 20 ml column of cyanogen bromide activated sepharose 4B (Pharmacia) previously linked to an excess of the primary antioestradiol antibody by conventional procedures. The column was washed with 50 mM Tris buffered saline until the eluate was free of protein and then the trapping antibody was eluted off at acid pH and neutralised by the addition of 200mM Tris buffer at pH7.6.

Fractions containing the trapping antibody were pooled and freeze dried to yield the solid trapping antibody (trapping antibodies against other small molecules such as progesterone may be similarly obtained). (DEAE ion exchange chromatography may be used in place of the protein A).

EXAMPLE 5

Trapping Antibody Against Methotrexate

Dihydrofolate reductase (DHFR) (5mg) was mixed with 100 ug methotrexate in 4 ml phosphate buffered saline (PBS) and the mixture dialysed against 2 liters of PBS twice at 4C. for eight hours each time. The dialysate was emulsified with 4 ml complete Freund's adjuvant and used to immunise a sheep by means of four intramuscular injections. One month later the animal received a similar series of injections but this time with incomplete Freund's adjuvant. A further month later the final immunisation was performed but this time without added adjuvant. Antisera were obtained and the IgG fraction obtained by sodium sulphate precipitation.

A rabbit was immunised with DHFR (1 mg) methotrexate (25 ug) IgG antibody obtained after the first immunisation of the sheep as above (5 mg) in 2 ml of PBS and emulsified with an equal amount of complete Freund's adjuvant. The animal was bleed one month later and antiserum prepared from the bleed.

A solution of highly purified DHFR of 100 ug/ml was made in PBS, 10 ul of this was added to 100 ul PBS containing 100,000 cpm of 3',5',7-3H Methotrexate (Amersham International catalogue number TRK.224). To this was added 10 ul of the immunoglobulin or antiserum under test and then 100 ul of a 1 mg/ml solution of unlabelled methotrexate was mixed in. This was 'zero time'. An aliquot was taken and the mixture kept at room temperature (21 C.) and further 10ul aliquots taken. Immediately after being taken each aliquot was applied to a Sephadex G25 column (ca 5 ml) equilibrated with PBS and the radioactivity remaining associated with the protein fraction in the eluant was subsequently determined. Graphs showing the ability of added antibody to stabilise the binding of the methotrexate to the DHFR were then drawn.

Table 4 shows the stabilisation achieved with salt fractionated sheep IgG. Table 5 shows the stabilisation achieved with antiserum obtained from the immunised rabbit.

TABLE 4

| Time (hrs) | Counts per Minute | |
| --- | --- | --- |
| | IgG from DHFR | Control |
| 0 | 800 | 866 |
| 1 | 432 | 602 |
| 2 | 283 | 564 |
| 3 | 235 | 541 |
| 4 | 220 | 495 |

TABLE 5

| Time (hrs) | Counts per Minute | |
| --- | --- | --- |
| | Antiserum against DHFR complex | Control |
| 0 | 570 | 670 |
| 1 | 491 | 377 |
| 2 | 410 | 208 |
| 3 | 351 | 183 |

EXAMPLE 6

Microtitre strips from Dynatech (Immunon II) were coated with a monoclonal antibody against oestradiol by allowing 1 ug of the antibody to soak in each well in 200 ul of 50 mM bicarbonate buffer pH 9.6 over-night at room temperature (21 C.). The wells were then washed four times with a glazing solution consisting of 0.2% casein in 50 mM Triss pH 7.4 (T7.4) and then a final time in the T7.4 alone.

Standard solutions of oestradiol ranging from 10 ug/ml to 10 fg/ml were then prepared in T7.4 and a standard curve constructed by the addition of 180 ul of each into separate wells (step 1) followed by incubation at room temperature for 30 minutes. 10 ul of tritiated oestradiol (containing 100,000 cpm) were then mixed into each well and the mixtures incubated for a further 15 minutes at room temperature after which 10 ul of a trapping antibody was mixed in and the mixture incubated for one hour at room temperature. This antibody had been raised by repeated immunisation of a rabbit with the monoclonal antibody mixed with excess oestradiol. After incubation, the contents of the wells were removed and the wells washed twice with T7.4 and 200 ul of a saturated solution of oestradiol in T7.4 was then added to all the wells. They were incubated for 30 minutes at room temperature and then washed four times with T7.4 containing 0.02% Tween 20. The individual wells were then separated from each other and their radio-active content determined by placing them in scintiallition fluid in vials and scintillation counting. A standard curve was then drawn to show the relationship between retained radioactivity and amount of added oestradiol standard.

Unknown samples were assayed using the same protocol but instead of adding standard in Step 1 above the samples were added. The concentration of oestradiol the samples contained were then obtained by means of relating the amount of retained radioactivity in their wells to concentration of oestradiol using the standard curve.

EXAMPLE 7

Monoclonal Trapping Antibody Against Oestradiol

Mice are immunised by repeated intraperitoneal injections of 100 ug of a primary monoclonal antibody against oestradiol mixed with 100 ug oestradiol and emulsified in complete Freund's adjuvant for the first immunisation, incomplete adjuvant for the second and no adjuvant for subsequent injections. The spleens of the animals are taken three days after the last injection and hybridomas made by means of standard techniques employing the cell line Ag8.

The hybridomas are screened by a two stage method as follows:

For the first step, the wells of Nunc microtitre plates are coated with lug each of affinity isolated sheep anti-$\mu$ antibody (Sigma Chemical Co Ltd London 1986 catalogue number M 1147) in 100 ul of 50 mM bicarbonate buffer pH 9.6 by leaving overnight at room temperature. The solution is removed and the wells glazed with 150 ul each of the same buffer containing 0.2% casein. The solution is left in the wells for 30 minutes and the wells then washed with 50 mM Tris pH 7.4 containing 0.02% Tween 20 (TT). 100 $\mu$l of the culture fluids under test are then placed in the wells and incubated at room temperature for a further hour. The solutions are then removed and the wells washed with TT. A blocking solution of 100 ul 50 mM Tris buffer pH 7.4 containing 1 ug of mouse IgM (Sigma Chemical Co - Mouse myeloma protein IgM, 1986 catalogue number M1520) is then added to wells and incubated at room temperature for 30 minutes. The solutions are removed and the wells washed four times with TT. A conjugate made by the methods of Voller, A., D. E. Bidwell and Ann Bartlett, Bull. World Health Organ., 53, 55 (1976) starting with 1.4 mg of the anti-oestradiol monoclonal antibody and 5 mg of alkaline phosphatase (Sigma Chemical Co Ltd London, 1986 catalogue number P 6774) is then diluted 1:750 in 50 mM Tris pH 7.4 and 100 ul added to each well and incubated at room temperature for one hour. The solutions are removed and the wells washed four times with TT. 100u of 10 mM para-nitrophenol phosphate on 50 mM bicarbonate buffer pH10.3 and containing 3.3 mM MgC12 is then added to each well and incubated at room temperature. The change in optical density at 405 nm is followed. Hybridomas producing culture fluids which give rise to a significant increase in optical density in the test (such as those producing an optical density over 1 unit when the negative controls were still at 0.4) are selected.

The clones which gave such positive results in the first part are then subjected to the second part of the screening method as follows:

Strips of microelisa wells (Immunlon II) are coated with a monoclonal anti oestradiol antibody by placing 100 ul of a solution containing 100 ug of the antibody in 50 mM bicarbonate buffer pH 9.6 and leaving them at 4 C. overnight. They are then glazed by a 30 minute incubation with 160 ul of the buffer containing 0.2% casein. Into each well is then added 100 ul of a solution of tritiated oestradiol (80,000 cpm per well) in 50 mM Tris pH 7.4. The wells are incubated for one hour at room temperature. 50 ul of the culture fluids under test are added to duplicate wells and culture fluid from the myeloma cell line added to control wells. The wells are incubated for a further 30 minutes. The solutions are shaken out and the wells washed four times with 50 mM Tris pH 7.4 containing 0.02% Tween 20. 100 ul of a saturated solution of oestradiol is then added to each well and one well of each duplicate immediately taken, the solution removed, the wells washed with TT and placed into scintillation fluid and the retained tritium label determined. The duplicates are incubated at room temperature for a further ten minutes and then similarly washed and measured. Hybridomas are selected as those producing culture fluid which are cloned and antibody produced in large amounts by means of standard techniques of ascites production in mice.

EXAMPLE 8

Use of Monoclonal Trapping Antibody

A radio-immunoassay for oestradiol was developed employing the above monoclonal antibody for oestradiol. Briefly this consisted of coating tubes with the monoclonal, glazing them to reduce non-specific background and then using them in a competitive assay in which sample competed for the solid phase bound antibody with radio-labelled oestradiol. The assay is a standard assay with incubation of the species followed by extensive washing of the tube prior to measurement of retained label. The addition of trapping monoclonal antibody after the normal incubation step followed by a short incubation (such as five minutes) improves the assay. (The trapping monoclonal antibody may also be added to the final wash solution employed for the extensive washing).

I claim:

1. A secondary antibody capable of stabilizing the binding of a small molecule of molecular weight 100–1500 to its binding protein which secondary antibody is capable of binding said binding protein in the presence of and in the absence of the small molecule but is not capable of binding said small molecule in the absence of said binding protein.

2. A secondary antibody according to claim 1 capable of stabilizing the binding of a small molecule of molecular weight 100–1500 to its primary monoclonal antibody which secondary antibody is capable of binding said primary monoclonal antibody in the presence of and in the absence of the small molecule but is not capable of binding said small molecule in the absence of said primary monoclonal antibody 3. A secondary antibody according to claim 2 which is a monoclonal antibody capable of stabilising the binding of a small molecule of molecular weight 200 to 1000.

4. A secondary antibody according to claim 3 wherein the small molecule is progesterone, oestradiol, oestratiol, oestrone sulphate, hydrocortisone, cortisone, testosterone, oestrogen, theophylline, digoxin or gentamicin.

5. A secondary monoclonal antibody according to claim 3 wherein the small molecule is a medicament.

6. A secondary monoclonal antibody according to claim 3 wherein the small molecule is a drug of abuse.

7. A secondary monoclonal antibody according to claim 6 wherein the small molecule is morphine.

8. A secondary monoclonal antibody according to claim 3 which has a k value of less than $10^2$ with respect to the small molecule 9. A secondary monoclonal antibody according to claim 8 which has a k value of at least $10^6$ with respect to the primary monoclonal antibody and the complex of the small molecule and primary monoclonal antibody.

10. A secondary monoclonal antibody according to claim 3 which is a complete immunoglobulin.

11. A secondary monoclonal antibody according to claim 3 which is a fragment of an immunoglobulin.

12. A secondary monoclonal antibody according to claim 3 in solid form.

13. A secondary monoclonal antibody according to claim 12 in the form of a freeze dried solid.

14. A secondary monoclonal antibody according to claim 12 within a closable container.

15. A method of preparing a trapping antibody according to claim 1 which comprises forming a complex between a small molecule of molecular weight 100–1500 and its binding protein, using that complex to raise antibodies and selecting antibodies which are capable of stabilizing the binding of the small molecule to its binding protein and which are capable of binding said binding protein in the presence of and in the absence of the small molecule but is not capable of binding said small molecule in the absence of said binding protein.

16. A competitive assay for a small molecule of molecular weight 100–1500 which comprises:
(a) introducing a sample of the small molecule to be determined and an amount of a labelled small molecule to a receptor for said small molecule in a manner which allows competition for the receptor to occur
(b) separating bound unlabelled small molecule from unbound labelled small molecule
(c) determining that fraction of the labelled small molecule which is bound or unbound;
wherein the improvement comprises (d) employing a trapping antibody to improve the binding of the small molecule and the labelled small molecule to the receptor.

17. An assay according to claim 16 wherein the receptor is a monoclonal antibody.

18. An assay according to claim 16 wherein the labelled small molecule is labelled with an isotope detectable by virtue of radioactive decay.

19. An assay according to claim 16 wherein the trapping antibody is employed after the competition between the small molecule and the labelled small molecule has taken place.

* * * * *